(12) United States Patent
Wang et al.

(10) Patent No.: US 9,040,574 B2
(45) Date of Patent: *May 26, 2015

(54) METHOD OF TREATING ANDROGEN INDEPENDENT PROSTATE CANCER

(71) Applicant: Natrogen Therapeutics International, Inc., New York, NY (US)

(72) Inventors: Longgui Wang, Flushing, NY (US); Simon K. Mencher, New York, NY (US); James P. McCarron, Jr., New York, NY (US)

(73) Assignee: Natrogen Therapeutics International, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/623,861

(22) Filed: Sep. 20, 2012

(65) Prior Publication Data

US 2013/0022609 A1 Jan. 24, 2013

Related U.S. Application Data

(63) Continuation of application No. 12/561,180, filed on Sep. 16, 2009, now abandoned, which is a continuation-in-part of application No. 12/548,083, filed on Aug. 26, 2009, now Pat. No. 8,394,847, which is a continuation of application No. 11/104,422, filed on Apr. 13, 2005, now Pat. No. 7,582,670, which is a continuation-in-part of application No. 10/754,547, filed on Jan. 12, 2004, now abandoned, and a continuation-in-part of application No. 10/864,458, filed on Jun. 10, 2004, now Pat. No. 6,933,315, which is a continuation of application No. PCT/US02/39866, filed on Dec. 13, 2002, and a continuation-in-part of application No. 10/021,589, filed on Dec. 13, 2001, now Pat. No. 6,566,341.

(60) Provisional application No. 61/097,280, filed on Sep. 16, 2008, provisional application No. 60/407,267, filed on Sep. 3, 2002.

(51) Int. Cl.
| | |
|---|---|
| A61K 31/7056 | (2006.01) |
| A61K 31/404 | (2006.01) |
| A61K 31/337 | (2006.01) |
| A61K 31/573 | (2006.01) |
| A61K 45/06 | (2006.01) |
| A61K 9/00 | (2006.01) |
| A61K 9/20 | (2006.01) |

(52) U.S. Cl.
CPC ............. *A61K 31/404* (2013.01); *A61K 9/0019* (2013.01); *A61K 9/2004* (2013.01); *A61K 31/337* (2013.01); *A61K 31/573* (2013.01); *A61K 31/7056* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 6,566,341 | B1 * | 5/2003 | Wang et al. | 514/25 |
| 6,933,315 | B2 * | 8/2005 | Wang et al. | 514/414 |
| 2002/0132792 | A1 | 9/2002 | Prien et al. | |

FOREIGN PATENT DOCUMENTS

| | | |
|---|---|---|
| WO | 99/30710 | 6/1999 |
| WO | 99/65884 | 12/1999 |
| WO | 03/051900 | 6/2003 |

OTHER PUBLICATIONS

English translation of Office Action dated Nov. 11, 2013, for corresponding Japanese Application No. 2012-092614.

* cited by examiner

*Primary Examiner* — Theodore R West
(74) *Attorney, Agent, or Firm* — Rodney J. Fuller; Booth Udall Fuller, PLC

(57) ABSTRACT

The present invention is directed to a method treating prostate cancer. The method comprises administering to a patient in need thereof at least one compound selected from N-methyl-Δ3,3'-dihydroindole-2,2' diketone; N-1-(β-D-O-triacetyl-xylopranosyl)-Δ3,3'-dihydroindole-2,2' diketone; and N-1-(β-D-O-triacetyl-xylopranosyl)-N'-methyl-Δ3,3'-dihydroindole-2,2' diketone. Preferably the compound is in an amount sufficient to inhibit growth, invasion, and/or metastasis of prostate cancer cells.

20 Claims, 6 Drawing Sheets

METHOD OF TREATING ANDROGEN INDEPENDENT PROSTATE CANCER

CROSS-REFERENCE TO RELATED PATENT APPLICATIONS

This patent application is a continuation of U.S. patent application Ser. No. 12/561,180, filed Sep. 16, 2009, which is based on and claims the benefit of U.S. provisional application No. 61/097,280, filed Sep. 16, 2008, and is also a continuation-in-part of U.S. patent application Ser. No. 12/548,083, filed Aug. 26, 2009, now U.S. Pat. No. 8,394,847, issued Mar. 12, 2013, which is a continuation of U.S. patent application Ser. No. 11/104,422, filed Apr. 13, 2005, now U.S. Pat. No. 7,582,670, issued Sep. 1, 2009, which is a continuation-in-part of U.S. patent application Ser. No. 10/754,547, filed Jan. 12, 2004 and U.S. patent application Ser. No. 10/864,458, filed Jun. 10, 2004, now U.S. Pat. No. 6,933,315, issued Aug. 23, 2005, which is a continuation of International Application PCT/US02/39866 filed Dec. 13, 2002, which claims priority to U.S. patent application Ser. No. 10/021,589, filed Dec. 13, 2001, now U.S. Pat. No. 6,566,341, issued May 20, 2003; International Application PCT/US02/39866 also claims the benefit of U.S. Provisional Application No. 60/407,267 filed Sep. 3, 2002, the content of each of which is expressly incorporated herein by reference thereto.

FIELD OF THE INVENTION

The invention relates to the treatment of advanced prostate cancer (AID), in particular, the hormone refractory and metastatic prostate cancer.

BACKGROUND OF THE INVENTION

Treatment of men with localized prostate cancer at diagnosis usually consists of potentially curative radical prostatectomy or radiation therapy (1).

However, a significant percent of these men progress to a condition known as advanced prostate cancer. Such "advanced" cancer requires additional therapy beyond surgery and/or radiation and many men develop metastatic disease. The treatment of choice for this condition is androgen ablation therapy which has been found to be palliative, not curative, although it can slightly improve the likelihood of survival. The majority of patients with advanced disease eventually progress to an androgen-independent stage (AID), also known as hormonal refractory prostate cancer (HRPC), which is unresponsive to further hormonal therapy, does not result in long-term survival, and whose best outcome is to maintain or to improve their quality of life.

Therapeutic options for patients with AID prostate cancer are limited, with lack of evidence for long-term survival. The current treatment for AID patients is chemotherapy with such agents as Docetaxel, Paclitaxel, Estramustine, Mitoxantrone, Vinorelbine and Doxorubicin, given alone or in combination. In some patients, clinically-effective chemotherapy may initially cause regression of a cancer, but the cancer invariably recurs due to cancer cells that recover, proliferate, and often metastasizes.

The chemotherapy standard of care, despite only minimal benefits, is Docetaxel. It provides only marginal improvements in survival for such patients (2, 3).

For any antitumor agent to be effective in AID refractory prostate cancer, it must arrest the proliferation of the cancer cells and/or also cause their death either by necrosis (i.e., cytotoxic anticancer agents/chemotherapy) or apoptosis (i.e., non-cytotoxic anticancer agents).

There is no pharmaceutical currently available, whether cytotoxic or non-cytotoxic, that can be considered as an effective treatment for this aggressive cancer. The median response to hormonal ablative therapy in patients with known metastatic disease has been reported to vary between 18 months and 3 years (4).

SUMMARY OF THE INVENTION

The present invention is directed to methods of effectively treating advanced stage prostate cancer, for example, AID refractory prostate cancer.

The method preferably comprises administering at least one compound selected from:

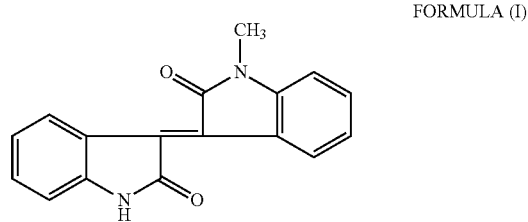 [SMILES: CN1C(=O)/C(=C2/C(=O)Nc3ccccc32)c2ccccc21]

Methylisoindigo (N-methyl-Δ3,3'-dihydroindole-2,2' diketone)

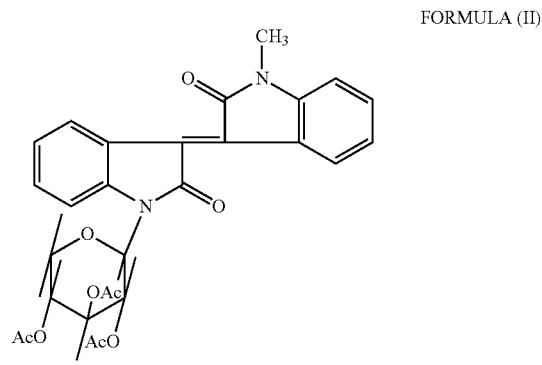

Pro-drug (N-1-(β-D-O-triacetyl-xylopranosyl)-N'-methyl-Δ3,3'-dihydroindole-2,2' diketone)

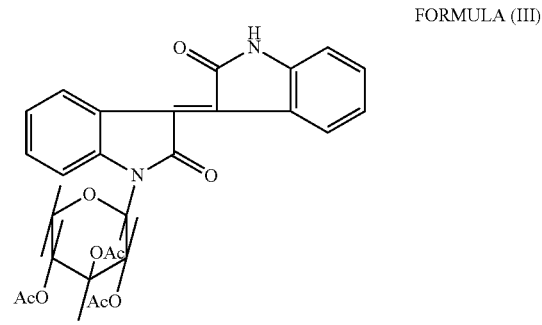

NATURA (N-1-(β-D-O-triacetyl-xylopranosyl)-Δ3,
3'-dihydroindole-2,2' diketone)

to a patient in need thereof, wherein the compound is in an amount sufficient to inhibit growth, invasion, and/or metastasis of prostate cancer cells. Preferably, the patient is tested and specifically identified as having androgen independent prostate cancer before administration of the compound.

In a preferred embodiment, the prostate cancer is androgen independent cancer and/or metastatic prostate cancer. The compounds of invention are suitable to induce apoptosis of androgen independent cancer cells when in a sufficient amount. Preferably the compound is in an amount sufficient to inhibit tumor invasion. In one embodiment, the compound is preferably in an amount sufficient to induce at least 10%, more preferably at least 20%, and most preferably at least 40% of cancer cells to become apoptotic. In another embodiment, the compound is preferably in an amount to inhibit at least 30%, more preferably 60%, and most preferably at least 75% of invasive cells.

Preferably the compound is administered in a pharmaceutical composition comprising a pharmaceutical acceptable carrier. Furthermore, preferably the patient is a male mammal (e.g., a horse, cow, dog, cat, sheep, etc.) and more preferable a male human.

Advantageously, the compounds of the invention can be administered in combination with chemotherapeutic agents, protein kinase inhibitors, topoisomerase inhibitors, mitotic kinesin inhibitors, histone deacetylase inhibitors, mTOR inhibitors, growth factor inhibitors, growth factor receptor inhibitors, transcriptional factor inhibitors, anticancer monoclonal antibodies, and/or glucocorticoid hormones. Preferred examples include administering the compounds of the invention in combination with paclitaxel and/or dexamethasone. Other examples of preferred chemotherapeutic agents include: alkylating agents, anti-metabolitic agents, antibiotics, anti-tubule agents, and anti-hormonal agents.

The protein kinase inhibitors preferably inhibit at least one of the following: cyclin-dependent kinases, tyrosine kinases, phosphoinositide 3-kinase PI3K/AKT, protein kinase C, casein kinases, MAP kinases, or Src kinases.

DETAILED DESCRIPTION OF THE PREFERRED EMBODIMENTS

Figure 1:
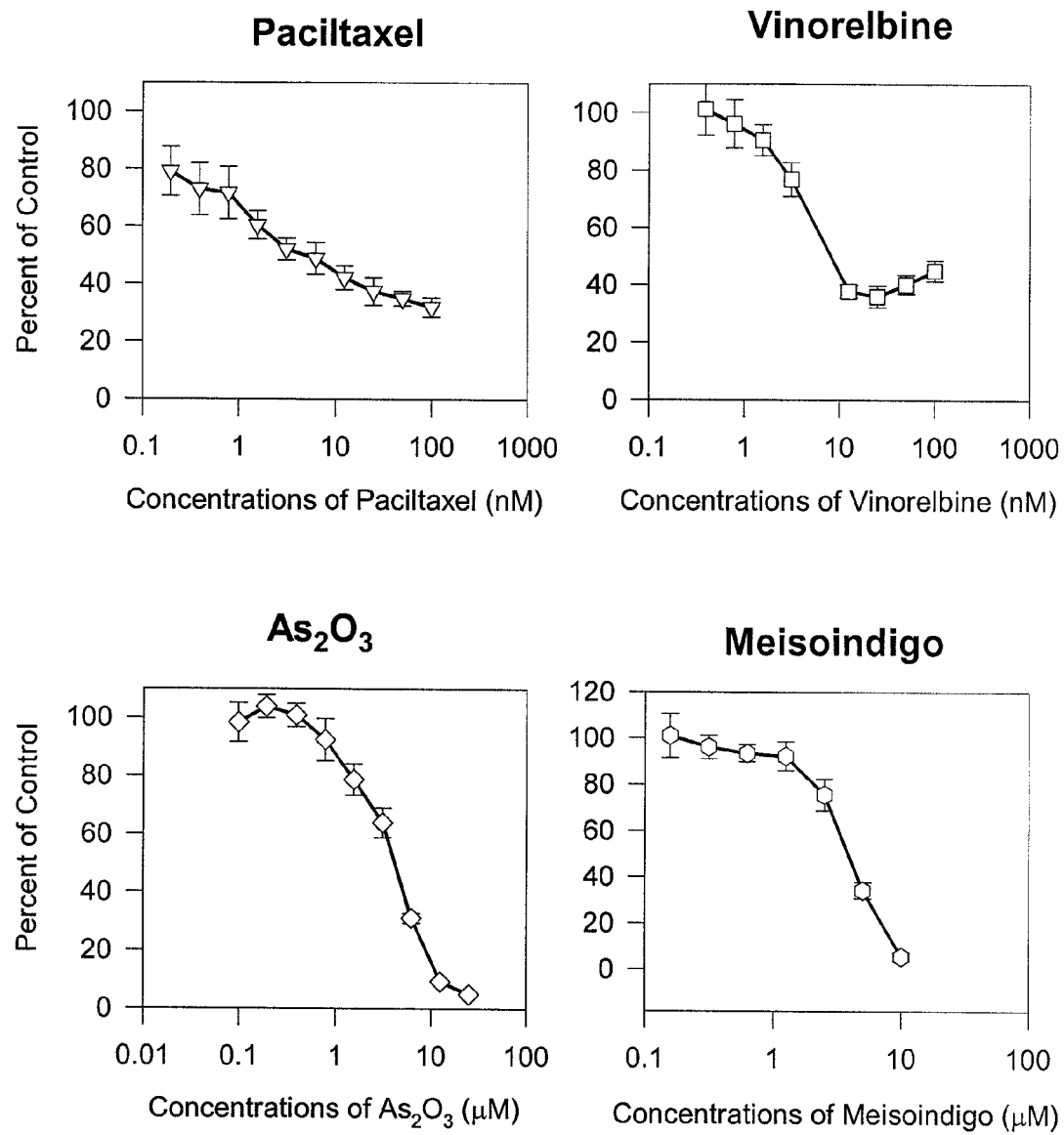
FIG. 1. Growth Inhibition of N-methylisoindigo on primary cultured human hormone refractory and metastatic prostate cancer cells. The hormone refractory and metastatic prostate cancer cells were isolated from human peritoneal fluid of a patient with advanced, hormone refractory, and spread prostate cancer. The primary cultured cells were cytogenetically confirmed by a pathologist as human prostate cancer cells. Growth inhibitory effects of N-methylisoindigo and other indicated agents on this primary cultured prostate cancer cells were determined by standard MTT.

The present invention is directed to methods of treating AID refractory prostate cancer using N-methylisoindigo, a non-cytotoxic drug.

The term "treatment" in the context of the present invention refers to any improvement in the clinical symptoms of the cancer, as well as any improvement in the well being of the patients, in particular an improvement manifested by at least one of the following: decreased tumor size, decrease in serum/plasma biomarkers, such as prostate specific antigen (PSA), prevention of tumor progression and metastasis (tumor stop growth and no new lesions are found). In one embodiment this is accomplished by administering an amount sufficient to induce cancer cell apoptosis, block cancer migration and invasion.

The therapeutically "effective amount" is the amount necessary to treat the androgen independent prostate cancer or relieve a symptom of the cancer. The effective amount can be readily determined, in accordance with the invention, by administering to a plurality of tested subjects various amounts of the active agent and then plotting the physiological response (for example an decrease of serum PSA) as a function of the amount. The amount above in which the therapeutic beneficial effects, such as PSA in prostate cancer, begin to decrease (but is still higher than normal value) is the "effective amount." Due to statistical distribution typically the "effective amount" is not a single parameter but a range of parameters.

Preferably the compound is in an amount sufficient to inhibit tumor invasion. In one embodiment, the compound is preferably in an amount sufficient to induce at least 10%, more preferably at least 20%, and most preferably at least 40% of cancer cells to become apoptotic. In another embodiment, the compound is preferably in an amount to inhibit at least 30%, more preferably 60%, and most preferably at least 75% of invasive cells.

It should also be noted that therapeutic benefits are typically realized by the administration of at least 1, 2, 3 or more of the compounds concurrently or sequentially. The compounds of the invention may also be combined with other therapies to provide combined therapeutically effective amounts. The compound can be administered, for example, in combination or in conjunction with additional agents, preferably anti-cancer agents. For example, in one embodiment the anti-cancer agent is administered separately by injection and the compound of the invention is administered orally, concurrently or sequentially with taxane and/or glucocorticoid hormones or other available chemotherapeutic agents.

Pharmaceutical Compositions and Dosage Forms

In a preferred embodiment, N-methylisoindigo is incorporated in a pharmaceutical composition that includes a pharmaceutically acceptable carrier. Advantageously, the composition may further include one or more anti-cancer agents. The anti-cancer agent can be any agent useful in treating cancer. Preferably the anticancer agent is an chemotherapeutic agent (alkylating agents, anti-metabolitic agents, antibiotics, anti-tubule agents, and anti-hormonal agents), a protein kinase inhibitor (including, but not limited to inhibitors of cyclin-dependent kinases, tyrosine kinases, phosphoinositide 3-kinase PI3K/AKT, protein kinase C, casein kinases, MAP kinases, and Src kinases), a topoisomerase inhibitor, a mitotic kinesin inhibitor, a histone deacetylase inhibitor, a mTOR inhibitor, a growth factor inhibitor, a growth factor receptor inhibitor, a transcriptional factor inhibitor, or an anticancer monoclonal antibody, or glucocorticoid hormones.

Examples of preferred chemotherapeutic agent include, but not limited to mechlorethamine (Embichin), cyclophosphamide (Endoxan), Myleran (Busulfan), chlorambucil, leukeran, paraplatin, cisplatin, carboplatin, platinol, Methotrexate (MTX), 6-mercaptopurine (6-MP), cytarabine (Ara-C), floxuridine (FUDR), fluorouracil (Adrucil), hydroxyurea (Hydrea), etoposide (VP16), actinomycin D, bleomycin, mithramycin, daunorubicin, taxol and its derivatives, vinca and its derivatives, bicalutamide (Casodex), Flutamide (Eulixin), Tamoxifen (Noluadex), Megestrol (Magace), and combinations thereof.

Examples of preferred a protein kinase inhibitor include midostaurin (PKC-412, CGP 41251, N-benzoylstaurosporine), UCN-01 (7-hydroxystaurosporine), bryostatin 1, perifosine, ilmofosine, Ro 31-8220, Ro 32-0432, GO 6976, ISIS-3521 (CGP 64128A) and the macrocyclic bis(indolyl) maleimides (LY-333531, LY-379196, LY-317615), as well as others underdevelopment, and combinations thereof.

Examples of preferred an anticancer monoclonal antibody include Cetuximab (Erbitux), Herceptin, and Bevacizumab (Avastin), or combinations thereof.

Examples of preferred glucocorticoid hormones include, but not limit to dexamethasone, prednisone, prednisolone, metyylprednisolone, hydrocoritisone.

In another preferred embodiment pharmaceutical composition comprises N-methylisoindigo. Typically the pharmaceutically acceptable carrier is an inert diluent.

The pharmaceutical compositions of the invention can take a variety of forms adapted to the chosen route of administration as discussed above. Those skilled in the art will recognize various synthetic methodologies that may be employed to prepare non-toxic pharmaceutically acceptable compositions of the compounds described herein. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide (DMSO).

Pharmaceutical compositions can be used in the preparation of individual dosage forms. Consequently, pharmaceutical compositions and dosage forms of the invention comprise the active ingredients disclosed herein. The notation of "the compound" signifies the compounds of the invention described herein or salts thereof.

Pharmaceutical compositions and dosage forms of the invention can further comprise a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, such as binder, surfactant, and lubricant, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, other excipients can be used.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; pills, caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their route of administration and animal being treated. For example, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

For a particular condition or method of treatment, the dosage is determined empirically, using known methods, and will depend upon facts such as the biological activity of the particular compound employed, the means of administrations, the age, health and body weight of the host; the nature and extent of the symptoms; the frequency of treatment; the administration of other therapies and the effect desired. Hereinafter are described various possible dosages and methods of administration with the understanding that the following are intended to be illustrative only. The actual dosages and method of administration or delivery may be determined by one of skill in the art.

Dosage levels of the order of from about 0.01 mg to about 100 mg, more preferably 0.1 mg to about 50 mg, and most preferably between about 0.5 mg to about 5 mg per kilogram of body weight in humans to treat AID prostate cancer, preferably per day. In another embodiment, between about 40 mg to about 500 mg, more preferably between about 60 mg to about 300 mg, and most preferably about 80 mg to about 240 mg are administered to a human per day. Dosage unit forms will generally contain between from about 5 mg to about 100 mg of the compound for human.

For illustrative purposes, dosage levels of the administered active ingredients in animals may be: intravenous, 0.1 to about 25 mg/kg; intramuscular, 0.5 to about 50 mg/kg; orally, 5 to about 150 mg/kg; intranasal instillation, 0.5 to about 10 mg/kg; and aerosol, 0.5 to about 100 mg/kg of host body weight. The dose level is usually about 10 times less in human than other animals.

Frequency of dosage may also vary depending on the compound used and whether an extended release formulation is used. However, in a preferred embodiment, the treatment of human AID prostate cancer is 3 times daily or less.

Preferably the compound is administered to the AID patients for a period of at least 16 week (4 week a cycle for 4 cycles). Applicants have discovered benefits of continuous extended administration of the compound to the AID patients being treated. In certain embodiments, administration may be for at least six month, at least a year or even longer. For certain AID conditions, the treatment may require continuous administration during the life of the patients being treated.

In another preferred embodiment, N-methylisoindigo, NATURA, and/or the pro-drug can also be used in combination with other therapies, including but not limited to surgery, radiation, or gene therapy.

Oral Dosage Forms

Pharmaceutical compositions of the invention that are suitable for oral administration can be presented as discrete dosage forms, such as, but are not limited to, tablets (e.g., chewable tablets), pills, caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredients in an intimate admixture with at least one excipient according to pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, NATURA1 and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103.TM, and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an active ingredient, anhydrous lactose, microcrystalline cellulose, polyvinylpyrrolidone, stearic acid, colloidal anhydrous silica, and gelatin.

Delayed Release Dosage Forms

Active ingredients of the invention can be administered by controlled release means or by delivery devices that are well known to those of ordinary skill in the art. Such dosage forms can be used to provide slow or controlled-release of one or more active ingredients using, for example, hydropropylm-ethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous, bolus injection, intramuscular, and intraarterial. Because their administration typically bypasses patients' NATURA1 defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

The present invention will now be illustrated by the following non-limiting examples. It is to be understood that the foregoing describes preferred embodiments of the present invention and that modifications may be made therein without departing from the spirit or scope of the present invention as set forth in the claims.

EXAMPLES

Example 1

Inhibitory Properties of N-methylisoindigo on Growth of Androgen Independent Prostate Cancer Drug Substance and Drug Products:

N-Methylisoindigo drug substance and drug product (capsules) was manufactured under cGMP guidelines and structure confirmed. The drug substance batch# NAT-0501, NAT-0502, NAT-0601 and drug product F070905-002 and B070918-002 were used in this study.

Reagents:

Paclitaxel, dexamethasone and other chemicals were obtained from Sigma Chemical Company (St. Louis, Mo.). Phosphorylation-specific antibodies were purchased from Cell Signaling Technology, Inc. (Danvers, Mass.).

Cell Cultures:

Human cancer cell lines of prostate LNCaP, DU 145 and PC-3 were purchased from American Type Culture Collection (Rockville, Md.). Androgen independent subline LNCaP AI was kindly provided by Dr. Ferrari (5) at NYU Cancer Institute, New York. The cells were cultured according supplier's instructions. Prostate cancer cells AIPC101 were isolated from human peritoneal fluid of a patient with advanced, hormone refractory, and spread prostate cancer. The primary cultured cells were confirmed cytogenetically by a pathologist as human prostate cancer.

MTT:

Growth inhibitory effects of N-methylisoindigo and other agents on human cancer cells were determined by standard MTT (3-(4,5-dimethylthiazol-2-yl)-2,5-diphenyltetrazolium bromide Test) as described previously (6). Cancer cells at exponential growth phase were aliquoted into 96-well plates at a density of 2500 or 5000 cells/200 µl per well in RPMI 1640 medium containing 10% FBS, and incubated overnight. The cells in the plates were then exposed to series of dilution of the indicated agents. After 72 h of incubation, 100 µl of the medium was removed from each of the wells and 50 µl of a 1 mg/ml solution of 3-(4,5-dimethylthiazol-2-yl)-2,5-diphenyltetrazolium bromide (MTT) was added to each well and the cells were incubated for additional 4 h. 200 µl of solution of 0.04 N HCl-isopropanol was added to each well to dissolve the black fromazan participates, and absorbance at 540 nm was measured on a 96-Well.

Western Blotting:

Protein levels of interest will be determined by Western blot as described previously (7). Fifty µg cellular extracts tumor cells were separated on a 7% or 10% SDS-PAGE, electro-transferred to nitrocellulose filters, and immunoblotted with antibodies as indicated, and β-actin for loading control.

Results and Discussion 1.1 Effects of N-methylisoindigo on Human Prostate Cancer Cells:

To explore if N-methylisoindigo is also effective on clinical hormone refractory and metastatic prostate cancer, prostate cancer cells AIPC101 isolated from human peritoneal fluid of a patient with advanced, hormone refractory, and spread prostate cancer was also tested for activity of N-methylisoindigo. FIG. 1 shows the effects of N-methylisoindigo and other clinical chemotherapeutic agents on growth of the primary cultured prostate cancer cells (AIPC101). Although this patient was highly resistant clinically to both hormonal and chemotherapy that led to eventually failure of the treatment, the cancer cells were response well to N-methylisoindigo. Exposure of the primary cultured cancer cells to N-methylisoindigo resulted in a significant growth inhibition in a concentration-dependent manner. The $IC_{50}$ of N-methylisoindigo was found to be approximately 4.0 µM, which are very closed to the $IC_{50}$ found in established hormone-dependent and independent prostate cancer cell lines above. It is noted that this primary cultured prostate cancer cells were found to be highly resistant to the treatment of both paclitaxel and virorelbine. For instance, the $IC_{50}$ of paclitaxel in LNCaP cells was found to be approximately 1 nM, however in this experiment the maximal inhibition of paclitaxel on AIPC101 was only to be about 60% at 100 times $IC_{50}$ of the drug in LNCaP cells. A similar result was also obtained when virorelbine. These findings were paralleled the outcomes of clinical treatment using paclitaxel for this patient. The primary cultured prostate cancer cells (AIPC101) were also response well to Arsenic trioxide. However, the concentrations were too high to be reached clinically under standard regimen of Arsenic trioxide.

1.2. Synergistic Growth Inhibitory Effects of N-methylisoindigo in Combination with Paclitaxel on Androgen Independent Prostate Cancer:

To explore if N-methylisoindigo is able to enhance activity of clinical available chemotherapeutic drugs used for prostate cancer, the commonly used antimicrotubule agent, paclitaxel (Taxol), was combined with N-methylisoindigo in three different sequential exposures:

Combination 1—exposure of LNCaP-AI cells to N-methylisoindigo+Taxol simultaneously for 6 days.

Combination 2—exposure of the cells to N-methylisoindigo first for 3 days followed by treatment with Taxol for additional 3 days (NTI→Taxol), or Combination 3—exposure of the cells to Taxol first for 3 days followed by treatment with N-methylisoindigo for additional 3 days (Taxol→NTI).

Exposure of the cells to either N-methylisoindigo or Taxol served as controls.

After exposure, cell growth was determined by MTT as described previously (8). The growth inhibition (1−T/C, Effect), median effect dose (Dm), and combination indexes (CI) were calculated, and analyzed using the computer program, CalcuSyn, of Biosoft edited by T. C. Chou, Memorial Sloan-Kettering Cancer Center, New York, and M. P. Hayball, of Biosoft, Cambridge, UK, (9). The combination index (CI) was used to evaluate the results of the combinations. A CI greater than 1 indicates the combination is antagonistic, CI equal to 1 indicates the combination is additive, and CI smaller than 1 indicates that the combination is synergistic (9).

The combination of the N-methylisoindigo, with the antimicrotubule agent, Taxol achieved a strong synergistic effect on LNCaP-AI prostate cancer growth. For example, the calculated Dm of N-methylisoindigo and Taxol alone against AI cells was found to be approximately 7.544 µM and 41.57 nM, respectively. However, when the two drugs were applied to the cancer cells simultaneously at ratio of 1000:1 (N-methylisoindigo:Taxol), Dm was significantly reduced to 0.783 µM and 0.780 nM, respectively (Table 1).

Figure 2:
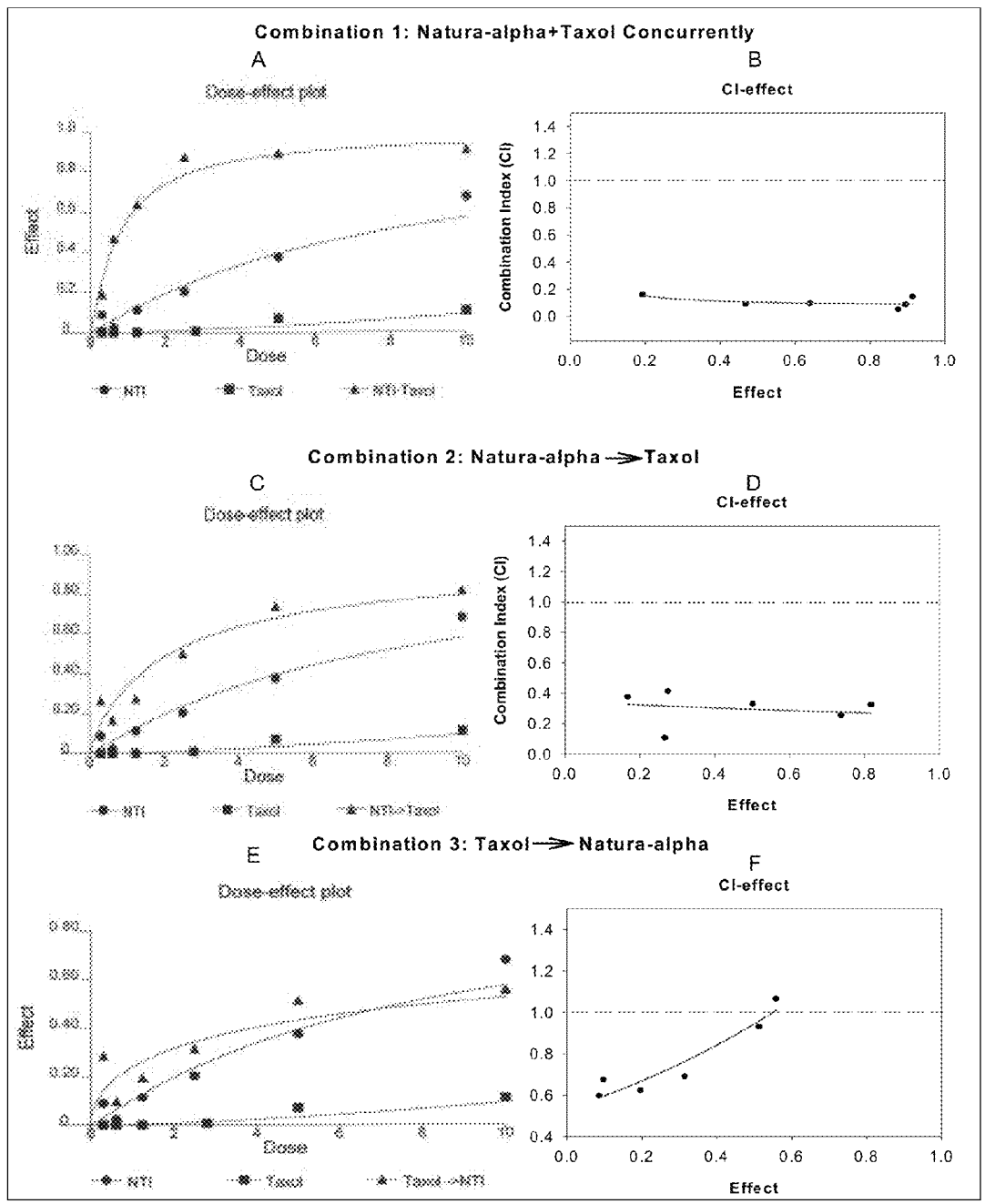
FIG. 2. Effects of N-methylisoindigo (NTI) and Taxol on cell growth of androgen independent prostate cancer (LNCaP AI) with different treatment regimen: Panel A, C, and E are Dose-effect curves, and B, D, and F are CI-effect curve. Dash line in Panel B, D, and F (CI=1) is the divider of outcomes of two-drug combination. CI value above the dash line indicates an antagonistic effect, below the line is a synergistic effect, and on the line implies an additive effect. A regression analysis of CI values versus effects in Panel B, D, and F were performed by Sigma plot 8, and the line direction indicates trend of a combination. Androgen independent LNCaP AI cells were treated simultaneously with NTI and Taxol (Combination 1); Panel C and D (Combination 2, NTI→Taxol): The cells were exposed to NTI first for 3 days followed by treatment of Taxol for additional 3 days; Panel E and F (Combination 3, Taxol→NTI): the cells were treated Taxol first for 3 days followed by the treatment of NTI for additional 3 days.

It is noted that as indicated by the Combination Index (FIG. 2, CI panels B, D, and F) and Dm values (Table 1), the effects of the combination are highly dependent on the sequence of the drug exposure. A strong synergistic growth inhibitory effect of LNCaP-AI cells was achieved when the cancer cells were exposed to N-methylisoindigo and Taxol concurrently (panel A and B, where CI at each concentration points were well below 1, whereas only a moderate synergism was observed when the cells were treated with N-methylisoindigo first for 3 days followed by Taxol treatment for additional 3 days. Notably, the trend of the combination became antagonistic when the cancer cells were exposed to Taxol for the first 3 days followed by exposure to N-methylisoindigo for an additional 3 days (FIG. 2, panels E and F). These findings strongly support our hypothesis that concurrently combined N-methylisoindigo with Taxol at a ratio of 1000 to 1 is most likely to achieve significant activity against both independent prostate cancer clinically.

TABLE 1

Dm of N-methylisoindigo (NTI) and Taxol in androgen independent prostate cancer cells with different treatment regimens

| Treatment Regimen | Dose of Median Effect | |
|---|---|---|
| | N-methylisoindigo (µM) | Taxol (nM) |
| Single agent | 7.544 | 41.577 |
| NTI + Taxol concurrently | 0.783 | 0.780 |
| NTI → Taxol | 2.159 | 2.160 |
| Taxol → NTI | 8.300 | 8.300 |

1.3. Growth Inhibitory Effects of N-methylisoindigo in Combination with Dexamethasone on Androgen Independent Prostate Cancer:

Dexamethasone has been reported to inhibits cell growth of AIPC (10, 11). To explore if the combination of N-methylisoindigo and dexamethasone produces desired therapeutic effects (additive or synergistic effects) on inhibition of AIPC growth, DU145 cells were exposed to N-methylisoindigo and dexamethasone alone or two drug in combination concurrently at ratio of 200:1 (N-methylisoindigo: dexamethasone) for 3 or 6 days. Cell growth was determined by MTT as described above. There was no growth inhibition observed when the DU-145 cells were exposed to dexamethasone alone for 3 days (data not shown) at concentration up to 100 nM, which made the analysis of the combination effect impossible. However, extending exposure time from 3 days to 6 days, a significant growth reduction by dexamethasone alone was obtained at relative high concentration. For example, this glucocorticoid hormone at concentration of 100 nM (39.2 ng/ml) inhibited growth of DU-145 by approximately 49%, which is consistent with a previous report (11). Considering relative low doses of dexamethasone used clinically (daily dose range from 0.5 to 8.0 mg) (12, 13), this high concentration (39.2 ng/ml dexamethasone) to inhibit prostate cancer growth may be not achievable. For example, peak plasma concentration of dexamethasone at 1 mg oral dose was found to be less than 6 ng/ml) (14) in human.

Figure 3:
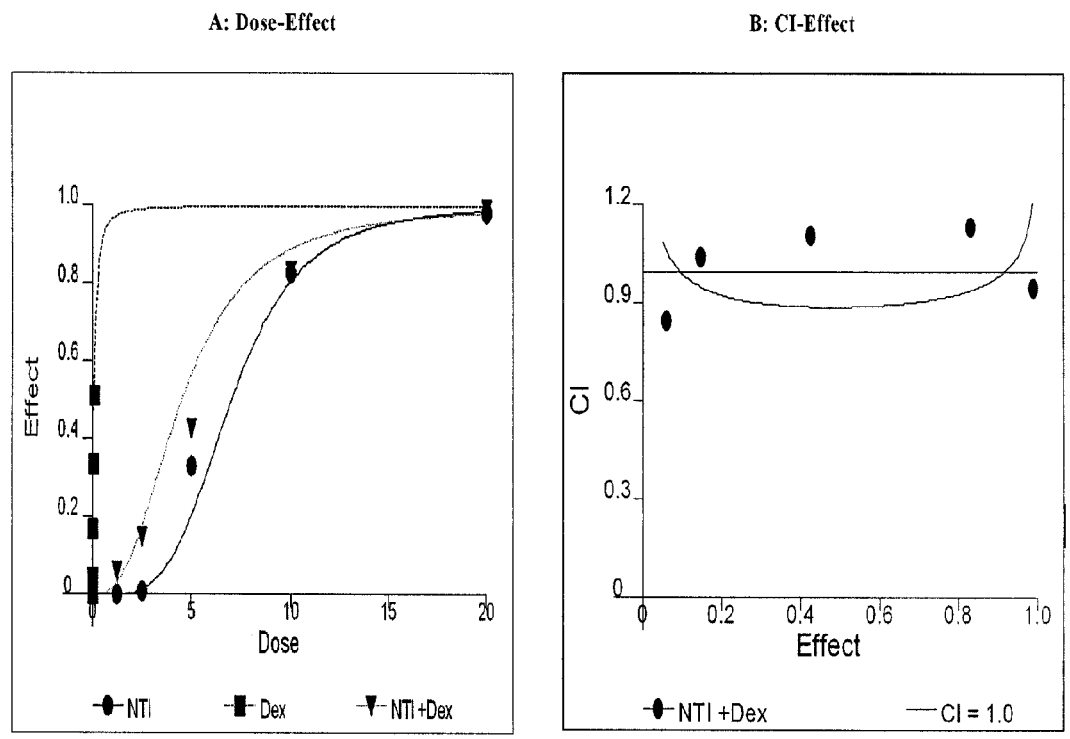
FIG. 3. Effects of N-methylisoindigo (NTI) and dexamethasone (Dex) on cell growth of androgen independent prostate cancer (DU145): DU145 cells were treated with N-methylisoindigo (●) or dexamethasone (■) or two agents together (▼) for 6 days. Panel A is Dose-effect curves, and B is CI-effect curve. Dash line in Panel B (CI=1) is the divider of outcomes of two-drug combination. CI value above the dash line indicates an antagonistic effect, below the line is a synergistic effect, and on the line implies an additive effect.

When dexamethasone was used in combination with N-methylisoindigo, an additive effect was obtained as indicated by the combination index (CI—equal to 1; FIG. 3, panel B). Although this combination achieved only an additive effect, it is noted that the dose reduction was significant, particularly that for dexamethasone. For example, the median effective concentration (Dm) for N-methylisoindigo and dexamethasone alone was 7.00 µM and 91.00 nM, respectively, however when the two drugs were combined together, the Dm of N-methylisoindigo was reduced from 7.00 µM to 4.50 µM and of dexamethasone from 91.00 nM to 22.48 nM. This finding suggests that the same efficacy can be achieved clinically at over a 4 fold decrease of a dose of dexamethasone when used in the presence of N-methylisoindigo. This is particular important for dexamethasone since high doses of the agent has been seen to cause significant side effects.

1.4 Effects on N-methylisoindigo-dexamethasone on Signaling

STAT3, a signal transducer and activator of transcription-3, and NF-κb have been demonstrated to play a critical role in both growth and progression of prostate cancer. Constitutive activation of Stat3 and NF-κb have been found in both in tumor cells, in immune cells, and in cancer related inflammation (15-18). Consequently, in the case of AIPC, it has been shown that STAT3 and NF-κb are constitutively active in the malignant prostate epithelium, and its activation is associated with high histological grade and advanced cancer stage.

Studies have been shown that dexamethasone inhibits activity of NF-κb in AIPC cells (10). We have observed that N-methylisoindigo inhibited activation of Stat3 in LPS-stimulated THP-1 cells. To explore whether combination of N-methylisoindigo with dexamethasone would enhance inhibition of Stat3 and NFκb, DU145 AIPC cells were treated with the indicated concentrations of either N-methylisoindigo or dexamethasone alone or two agents together for 72 hrs, and the activities of Stat3 and NF-κb were determined by Western blot using phosphor-specific antibodies against pStat3 and p65NF-κb.

Figure 4:
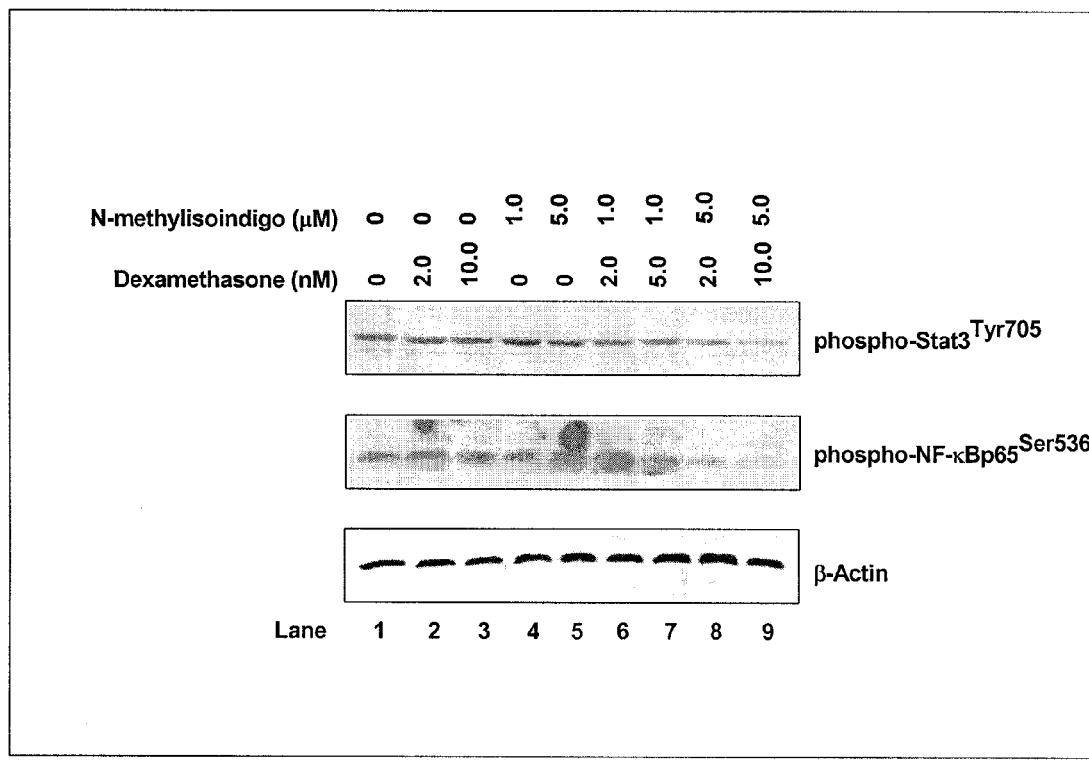
FIG. 4. Effects on N-methylisoindigo-Dexamethasone on Stat3 and NF-κb Signaling: DU145 cells (a hormone refractory prostate cancer cell line) at exponential growth phase were exposed for 72 hours to either dexamethasone (DEX), or N-methylisoindigo alone, or DEX plus N-methylisoindigo at indicated concentrations. The cells were then harvested, washed, and total proteins extracted. Fifth μg of the proteins were subjected to SDS-PAGE, electro-transferred to Ninon membrane, and immune-blotted with antibodies specifically against phosphor-Stat3$^{Tyr705}$, phosphor-NFκbp65$^{Ser536}$, cyclin D1 or β-Actin as a loading control.

As shown in FIG. 4, no effects of either DEX or N-methylisoindigo alone on activation of Stat3 and NF-κb were observed at given concentrations (lane 1 to 6), however, when DEX combined with N-methylisoindigo (lane 7 to 9), the levels of phosphor-Stat3$^{Tyr705}$, and phosphor-NF-κBp65$^{Ser536}$, were significantly decreased. The finding indicates that combination of N-methylisoindigo and dexamethasone enhanced their inhibitory activity on both Stat3 and NF-κb, which in turn, may not only inhibit AIPC cell growth, but prevents their progression and metastasis since increasing evidence have demonstrated that inflammatory mediators such as NF-κb, Stat3, IL-1β, and IL-6, have been linked to prostate cancer carcinogenesis, progression and metastasis (19, 20).

Example 2

Induction of Apoptosis by N-methylisoindigo in Prostate Cancer Cells

Method
Reagent:
N-Methylisoindigo was from the same resource as described in Example 1, and was prepared at 20 mM in DMSO (dimethyl sulfoxide), and stored at −20° C. until use.

Cell Culture and Treatment:
LNCaP and LNCaP AI were from the same resource as described in Example 1. LNCaP and LNCaP AI cells at exponential growth phase were treated with different concentrations (0 to 20 µM) of N-methylisoindigo for 48 hours. Analysis of cell cycle was performed using a Becton-Dickinson FACScan flow cytometer with the methods described previously (21). The cells were fixed with 80% ethanol at 4° C., and incubated on ice before the DNA was stained with propidium iodide (50 µg/ml).

Results and Discussion
Tables 2 and 3 shows the effects of N-methylisoindigo on cell cycle and induction of apoptosis in both androgen dependent and independent prostate cancer. N-methylisoindigo significantly induced apoptosis of both androgen dependent and independent prostate cancer cells in a concentration-dependent manner. The apoptotic cells were found to over 35% in LNCaP cells and almost 19% in LNCAP-AI cells when they were treated with 20 μM of N-methylisoindigo for 48 hours. It is also worth to note that different cell cycle blockages between LNCaP and LNCaP-AI cells by N-methylisoindigo were observed in this experiment. S phase of LNCaP cells were increased in a concentration-dependent manner after N-methylisoindigo treatment, indicating a blockage occurred at transition from G1 phase toward S phase of the cells. However, LNCaP-AI cells were arrested at G1 by N-methylisoindigo treatment under the same experimental conditions. These cell cycle interruptions in androgen dependent and independent prostate cancers are different from that in leukemia where at lower concentrations (<5 μM) leukemia cells were arrested at G1 by N-methylisoindigo (22), and at higher concentrations (>10 μM) the cells were arrested at S phase (23), indicating responses of prostate cancer cells to N-methylisoindigo are different from leukemia cells.

TABLE 2

Induction of hormone-dependent prostate cancer (LNCaP) apoptosis by N-methylisoindigo

| N-methylisoindigo (μM) | LNCaP Cells | | | |
|---|---|---|---|---|
| | G1 (%) | S (%) | G2 + M (%) | Apoptotic Cells (%) |
| 0 | 78.19 | 1.27 | 20.54 | 1.78 |
| 2 | 77.87 | 15.01 | 7.12 | 2.05 |
| 10 | 75.92 | 16.39 | 7.69 | 4.66 |
| 20 | 63.53 | 25.43 | 11.04 | 35.64 |

TABLE 3

Induction of hormone-independent prostate cancer (LNCaP-AI) apoptosis by N-methylisoindigo

| N-methylisoindigo (μM) | LNCaP-AI | | | |
|---|---|---|---|---|
| | G1 (%) | S (%) | G2 + M (%) | Apoptotic Cells (%) |
| 0 | 55.26 | 35.47 | 9.27 | 3.46 |
| 2 | 60.91 | 26.74 | 12.34 | 7.53 |
| 10 | 66.63 | 21.97 | 11.40 | 8.61 |
| 20 | 69.01 | 23.47 | 7.52 | 18.73 |

Example 3

Inhibition of N-methylisoindingo on Invasion of Androgen Independent Prostate Cancer Reagent:
N-Methylisoindigo was from the same resource as described in Example 1, and was prepared at 20 mM in DMSO (dimethyl sulfoxide), and stored at −20° C. until use.

Cell Culture and Treatment:
LNCaP and LNCaP AI were from the same resource as described in Example 1.

Invasion Assay:
Effect of N-methylisoindigo on invasive activity of LNCaP and LNCaP-AI cells was determined via the transwell Madrigal invasion assay (Growth Factor Reduced Matrigel Invasion Chamber). Transwell inserts were coated with Madrigal (Growth Factor Reduced) for 2 hours at room temperature. The inserts were then washed with PBS and used immediately. The inserts are precoated by the company. After rehydration of the insert with medium for 2 hours, LNCaP-AD and LNCaP-AI cells at their exponential growth phases were added to the upper chamber at density of $1\times10^4$ cells in 500 ul medium in the presence or absence of indicated concentration of N-methylisoindigo, NATURA, or the pro-drug and incubated at 37° C. for 48 hours. After the incubation, the non-invading cells were removed from upper chamber with a cotton swab, and the invading cells adherent at the bottom of membrane were fixed, stained, and counted by tallying the number of cells in 3 random fields under the microscope. Data are adjusted by growth condition, and expressed as mean of migrating cells in 3 fields+/−SD.

Results and Discussion

The ability of tumor cells to invade is one of the hallmarks of the metastatic phenotype. To detail the mechanisms by which tumor cells acquire an invasive phenotype, the Matrigel invasion assay was developed for use in the laboratory. Thus, there is a means to study in the laboratory, the ability of a cancer cell to metastasize. These cell invasion assays have been developed for quantitative study under well-established in vitro conditions of the ability of cultured cells to penetrate biological barriers such as basement membrane. The technology is based on Engelbreth-Holm-Swarm (EHS) sarcoma (mouse cancer of the connective and structural tissues). Cultured cells behave as they do in vivo and so Matrigel provides a physiologically relevant environment for studies of cell morphology, biochemical function, migration or invasion, and gene expression. Matrigel contains not only basement membrane components (collagens, laminin, and proteoglycans) but also matrix degrading enzymes, their inhibitors and growth factors. Invasion of tumor cells into Matrigel has been used to characterize involvement of ECM receptors and matrix degrading enzymes which play roles in tumor progression.

To examine whether N-methylisoindigo inhibits the invasive potential of prostate cancer cells, invasive activity of LNCaP and LNCaP-AI cells was determined via the transwell Madrigal invasion assay. Transwell inserts were coated with Madrigal (growth factor reduced) at room temperature for 2 hrs. The inserts were then washed with PBS and used immediately. LNCaP and LNCaP-AI cells at their exponential growth phases were added to the upper chamber at density of $1\times10^4$ cells/per well in 500 ul medium in the presence or absence of indicated concentration of N-methylisoindigo and incubated at 37° C. for 48 h. After the incubation, the non-invading cells were removed from upper chamber with a cotton swab, and the invading cells adherent at the bottom of membrane were fixed, stained, and counted by tallying the number of cells in 3 random fields under the microscope. Data are adjusted by growth condition, and expressed as mean of migrating cells in 3 fields+/−SD.

Figure 5:
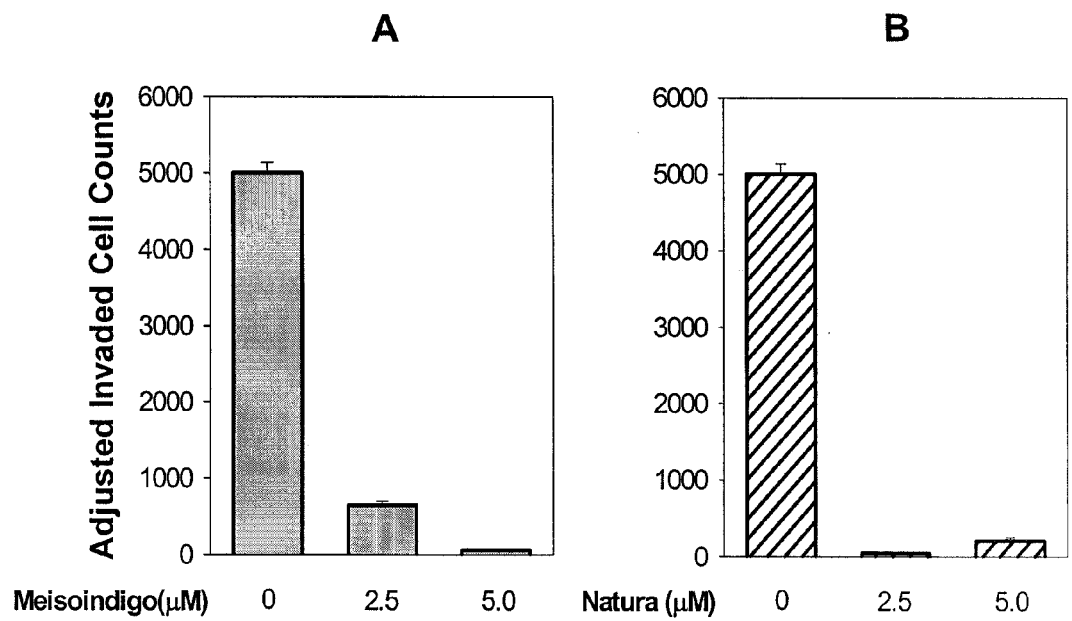
FIG. 5 Inhibitory effects of N-methylisoindigo and NATURA on invasion of LNCaP-AI cells. The invasive activity of LNCaP-AI cells was determined via the transwell matrigel invasion assay. Transwell inserts were coated with matrigel (Growth Factor Reduced) for 2 h at room temperature. The inserts were then washed with PBS and used immediately. LNCaP-AD and LNCaP-AI cells at exponential growth phase were added to the upper chamber at density of $1\times10^4$/per well in 500 ul medium in the presence or absence of indicated concentration of N-Methylisoindigo and NATURA. The cells were incubated at 37° C. for 48 h. After the incubation, the non-invading cells were removed from upper chamber with a cotton swab, and the invading cells adherent to the bottom of membrane were fixed, stained, and counted by tallying the number of cells in 10 random fields under microscope. Data are adjusted by growth condition, and expressed as mean of migrating cells in 3 fields+/−SD.

Results showed that invasive capacity of LNCaP cells were highly limited. There were only a few cells that migrated (data not shown). In contrast, LNCaP-AI cells showed strong invasive potentials. Over 4000 cells/field were found migrated during 48 h culture only in the presence of androgen, indicating that it was androgen dependent. Notably, the invasive capacity of LNCaP-AI cells was strongly blocked by N-methylisoindigo in a concentration-dependent manner (FIG. 5). Inhibitions of invasive LNCaP-AI cells by N-methylisoindigo were reached over 87% and 99% at concentrations of 2.5 μM and 5.0 μM (FIG. 5), respectively. These data demonstrated that inhibition of prostate cancer cell proliferation and metastasis can be achieved by restricting energy supplies through application of cdk inhibitors.

Example 4

Effect of N-methylisoindigo on Xenograft LNCaP AI Prostate Cancer

Reagent:

N-Methylisoindigo was from the same resource as described in Example 1.

Cell Culture and Treatment:

LNCaP AI cells were from the same resource as described in Example 1.

Xenograft Models:

Androgen independent LNCaP AI prostate cancer cells, mixed with Matrigel (Becton Dickinson, Bedford, Mass.) at a ratio of 1:1 were inoculated into the bilateral flanks of 4-5 weeks male Nu/Nu Balb/c athymic nude mice by subcutaneous injection. The tumor growth and volume was monitored every 3 days as described by Taneja et al (24). When the prostate tumor grew to a diameter of 4-8 mm (4-5 weeks), animals were randomly divided into 2 groups, 10 mice each, according to tumor size. One group of animals was treated with drug vehicle only for control, and another group was treated with N-methylisoindigo at dose of 100 mg/kg by gavage, once a day, 5 days a week until the diameter of tumors in control group reached 15 mm. The tumor growth was monitored daily and tumor size recorded every three days. The tumor volume was calculated as 1×d×h×0.52 (24).

Results and Discussion

Figure 6:
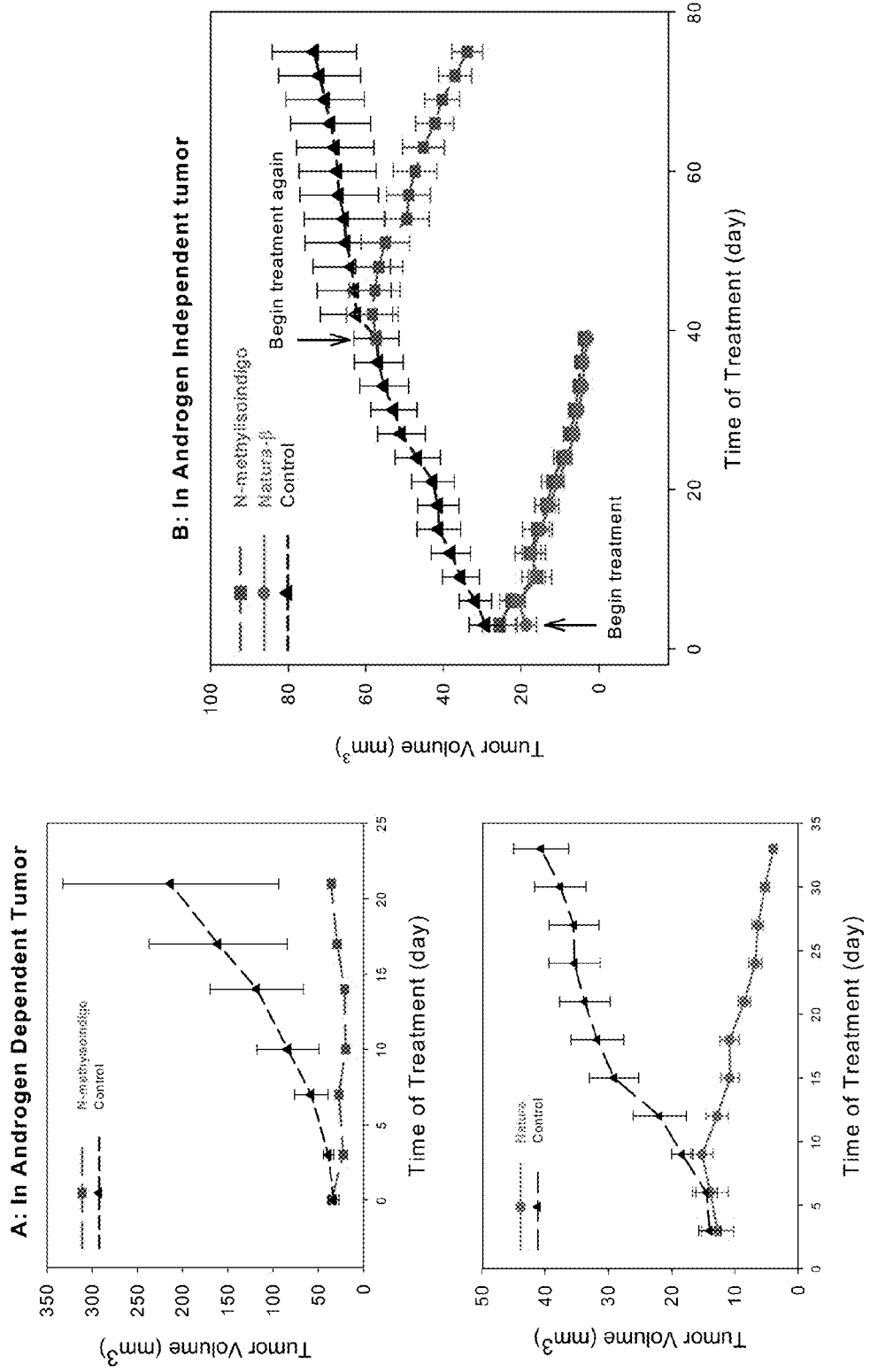
FIG. 6. Inhibition of N-methylisoindigo and NATURA (1-(β-D-O-triacetyl-xylopranosyl)-isoindigo) on human androgen-dependent and independent prostate cancer xenografts in nude mice: Androgen dependent LNCaP (panel A) and independent LNCaP AI (panel B) prostate cancer cells were transplanted subcutaneously into the flank region of male nude mice. After the prostate tumor grew for 4-5 weeks, animals were randomly divided into two groups (10 animals per group), according to tumor size. A suspension of N-methylisoindigo and NATURA was given at equal molecular dose (100 mg/kg for N-methylisoindigo and 189 mg/kg for NATURA) by gavage once a day, 5 days a week for indicated period of time. The tumor size was measured blindly every 3 days, and tumor growth curves (tumor size versus time) were plotted. It is noted, on day 39, the androgen independent tumors in drug treated group became too small to be accurately measured (panel B), thus the treatment was terminated. On the same day, the animals in vehicle-controlled group were equally split into two groups, one group continuous served as control, and another was given N-methylisoindigo as described above.

In an androgen dependent and independent prostate xenograft models, LNCaP and LNCaP AI prostate cancer cells were injected subcutaneously into the flank region of male nude mice. After the prostate tumor grew for 4-5 weeks, animals were randomly divided into two groups (10 animals per group) according to tumor size. A suspension of N-methylisoindigo (prepared using N-methylisoindigo powder and N-methylisoindigo capsules) was given at dose of 100 mg/kg by gavage once a day for 5 days a week for indicated period of time. The tumor size was measured blindly every 3 days, and tumor growth curves (tumor size versus time) were plotted. As shown in FIGS. 6A and B, tumor growth in N-methylisoindigo treated groups was almost completely halted whereas tumors in vehicle treated group increased grow exponentially. N-methylisoindigo was particularly effective in androgen independent tumor (panel B). Since on day 39, the AI tumors in N-methylisoindigo treated group became too small to be accurately measured, the treatment was terminated. On the same day, the animals in vehicle-controlled group were equally split into two groups, one group continuous served as control, and another was given N-methylisoindigo as described above. As shown in panel B, even at later stage of the androgen independent tumor, N-methylisoindigo was still very effective. It not only completely halted the tumor growth, but significantly reduced the tumor volume. For example, on day 78, the average of tumors in N-methylisoindigo treated group was shrunk by 53%. It is noted that growth of LNCaP AI cell is much slower than its parental LNCaP cells.

Example 5

Therapeutic Activity of N-methylisoindigo on Advanced Androgen Independent and Metastatic Prostate Cancer It is noted that this clinical trial was under US FDA IND# 104191.

Drug Substance and Drug Products:

N-Methylisoindigo drug substance and drug product (capsules) was manufactured under cGMP guidelines and structure confirmed. The drug substance batch# NAT-0601 and NAT-0801 and drug product F071126-001 and F090114-002 were used in this study.

Patient History

The patient is an 87 year old man with hormone refractory prostate cancer metastatic to liver, bone and lymph nodes. His prostate cancer was diagnosed in late 2002 by needle biopsy performed for an elevated PSA (9 ng/mL). Initial treatment was external beam radiation (8100 cGy) completed in April of 2003. In early 2005, a rising PSA resulted in initiation of androgen ablation initially with Casodex and subsequently with Lupron which has been continued to the present time. Because of recurrent PSA rise, the anti-androgen Nilandron was administered in October 2006. This medication had a good response (PSA decline 24 to 0.81) until August 2007 when it was discontinued due to a further PSA elevation. Nizoral was then instituted (September 2007) but was stopped after one month due to liver toxicity. With continuing rise of PSA (50), Lu-J591 (an anti PSMA monoclonal antibody) was injection on Dec. 19, 2007 and Jan. 3, 2008. PSA thereupon initially stabilized in the range 40 to 60, but was seen to be elevated to 135 in August of 2008 when liver metastases were also noted via CAT scan. Taxotere infusions were then administered on 3 separate occasions. Despite relative stability of laboratory tests, a follow up CAT scan disclosed further progression of liver metastases. Chemotherapy protocol was then changed to Etoposide/Cisplatin. This combination, given the week of Nov. 24, 2008 resulted in a continuing feeling of malaise as well as nausea and vomiting. Additional infusions of these agents were planned for mid-December, 2008, but the patient decided to terminate this treatment and switch to NATURA-alpha treatment because of his inability to tolerate the then current side effects. The patient also experienced pain in his right shoulder.

Laboratory Studies

Before initiating treatment with N-methylisoindigo, various laboratory tests were performed, including hematology and biochemistry on Comp Metab panel; hepatic function panel; prothrombin time; PTT, and PSA.

The patients PSA was seen to increase significantly from 128 ng/mL on Nov. 25, 2008 to 176 ng/mL on Dec. 15, 2008 respectively. Serum alkaline phosphostase was high at 199 U/L on Dec. 18, 2008. Other laboratory test abnormalities were also observed as shown in Table 4.

TABLE 4

List of parameters out of normal range-(Dec. 18, 2008)

| Parameter | Observed | Reference range | | Remark* |
|---|---|---|---|---|
| Sodium | 133 | 135-146 | mmol/L | L |
| Chloride | 97 | 98-110 | mmol/L | L |
| Alkaline phosphotase | 199 | 40-115 | U/L | H |
| RBC | 3.30 | 4.20-5.80 | Mill/mcL | L |
| Hemoglobin | 10.60 | 13.2-17.1 | g/dL | L |
| Hematocrit | 31.9 | 38.5-50.0% | | L |
| RDW | 20.0 | 11.0-15.0% | | H |
| MPV | 6.8 | 7.5-11.5 | fL | L |
| Monocytes, absolute | 1494 | 200-950 | cells/mcL | H |
| Myelocytes, absolute | 166 | 0-0 | cells/mcL | H |
| Uncleated RBC | 1 | 0-0/100 | WBC | H |
| ESR, Westergren | 72 | 0-20 | mm/hr | H |
| Uncleated RBC, Absolute | 83 | 0-0 | cells/mcL | H |
| PSA, Total | 176.27 | <4.0 | ng/mL | H |

*L: Low; H: High

Imaging Studies

Anterior and posterior whole body images were also obtained on Dec. 18, 2008, 2 hrs after IV administration of 26.6 mCi of Tc99m-MDP.

The scan showed multiple osseous metastatic lesions in the anterior and posterior ribs, thoracic and upper lumbar spine, left anterior iliac crest and posterior lioac bones. Compared with the previous scan on Nov. 3, 2008, changes were that several lesions increased prominence as follow: left posterior $5^{th}$ rib, right posterior $6^{th}$ rib, right posterior $9^{th}$ rib, thoracic vertebral bodies 7 and 10.

A CT scan of the chest, abdomen and pelvis was performed on Dec. 18, 2008 at contiguous 3.75 mm axial intervals following the administration of oral and intravenous contrast (120 cc of Visipaque 320). Coronal reformats were performed for further evaluation of intra-abdominal organs.

The CT scan identified patchy ill-defined ground glass opacities in left lower lobe. There were scattered calcified granulomas, consistent with prior granulomatous disease. As compared with the CT study on Nov. 3, 2008, a significant progression of disease was observed as reflected by enlarging metastatic lesions throughout the liver, new hilar lymphadenopathy with increasing size of prominent retroperitoneal lymph nodes, and increased prominence of several bony metastases. In addition, there were grossly stable ill-defined ground glass opacities in the left lower lobe, likely infectious or inflammatory in etiology.

Diagnosis

On the basis of disease history and the most recent data from lab, and imaging studies, a diagnosis was made of advanced hormone refractory prostatic adenocarcinoma with metastases to lymph nodes, bone, and liver.

Concomitant Medications:

On Dec. 17, 2008, before N-methylisoindigo treatment, the patient had taken the following medications:

Fosamax 70 mg, one tablet a week
Levothyroxine (Synthroid), 0.15 mg, once a day
Lupron 22.5 mg, once a month
Calcium with Vitamin D, 500 mg, twice a day
Desmopressin 0.2 mg, once a day at bedtime
Hydrocodone/APAP 5/500 mg, qid as needed.

Patient Treatment

Under IND no. 70,984, N-methylisoindigo was to be administered in 4 week cycles at an initial oral dose of 40 mg bid (twice a day) for three weeks, followed by 1 week off. Since the patient tolerated N-methylisoindigo at the oral dose of 40 mg bid, the treatment regimen was amended after IRB approval, to a dose of 80 mg bid continuously with an eventual increase to 200 mg daily in divided/irregular doses, as described below.

Administration of N-methylisoindigo was started on Dec. 21, 2008 at initial daily dose of 80 mg (40 mg, bid) until Jan. 3, 2009. The dose was then increased to 160 mg daily (80 mg, bid.) from Jan. 3, 2009 to Jan. 21, 2009, and further increased to 200 mg (80, 20, 80 mg) from Jan. 22, 2009 to Feb. 14, 2009. The dose was lowered to 80 mg daily dose from Feb. 15, 2009 to Mar. 6, 2009, and drug holidays were given from Mar. 7, to Mar. 11, 2009. The treatment was restored on Mar. 12, 2009, initially with a daily dose of 80 mg (Mar. 12, to Mar. 20, 2009), and then increased to a daily 160 mg until Apr. 7, 2009.

Because of the threat of cord compression of osseous metastatic tumors in all spinal segments, as well as circumferential dural thickening with canal stenosis at T1 to T4 and epidural extension at T6, dexamethasone (4 mg, bid) and radiation therapy (6750 cGy) were initiated with resultant improvement in pain and preservation of neurological function noted on Jan. 6, 2009.

Administration of dexamethasone was started on Jan. 6, 2009 with an initial daily dose of 8 mg (4 mg, bid), and then lowered to daily 4 mg (2 mg bid), and stopped on Jan. 22, 2009. The treatment was restored on March 12 at a daily dose of 4 mg (2 mg, bid), and reduced to daily dose of 2 mg (1 mg bid) from Mar. 31, to Apr. 1, 2009 and then increased to a daily dose of 8 mg (2 mg, qid) until the last examination on Apr. 7, 2009.

Other Treatment

Lupron was given in Jan. 15, 2009 at dose of 7.5 mg.

Criteria of Evaluation of Treatment Response and Toxicity

The PSA and appropriate scans (bone scan, CT scan of chest, abdomen and pelvis) of the patient were to be performed at the end of each 4 week cycle. Results of the radiographic tests performed before N-methylisoindigo and dexamethasone treatment on Dec. 18, 2008 were to be used as the baseline for evaluation. PSA rises in the absence of symptomatic or radiographic progression was to be followed with the goal of determining progression after 32 weeks exposure. Treatment benefit was to be evaluated for the first time at the end of the second cycle, and thereafter every cycle following NCI guidelines (25). The patient was to be urged to stay on study until completion of at least 16 weeks of treatment (4 cycles). Treatment progression was defined as worsened liver metastasis or appearance of new painful bone metastases.

Toxicities were to be graded according to the National Cancer Institute Common Terminology Criteria for Adverse Events, version 3.0 (NCI CTCAE v.3.0).

Results and Discussion

Biological Response

During the three treatment cycles (12 weeks) of N-methylisoindigo since Dec. 21, 2009; laboratory testing and imagining examinations have been performed. The value of alkaline phosphotase (APL) generally decreased during this period, for example on Dec. 28, 2009 it was 377 U/L, and it decreased to 123 U/L on Mar. 30, 2009. Serum PSA on the other hand, was initially 270 ng/mL on Jan. 2, 2009 and decreased to 160 ng/mL on Jan. 20, 2009; and then increased to 294 ng/mL on Mar. 20, 2009. The initial decrease of PSA is thought probably due to dexamethasone treatment as observed previously (12, 26). The decrease of ALP may reflect improvement of liver and bone metastases.

Assessment of Target Response

Target response has been evaluated by anterior and posterior whole body images (bone scan) and a CT scan of the chest, abdomen and pelvis studies at end of each cycle. These studies showed that overall tumor burden improved. CT scans at end of each cycle showed that metastatic disease within the liver improved as compared with Dec. 18, 2009 (before N-methylisoindigo/dexamethasone treatment). Multiple metastatic lesions within the liver were unchanged in number but decreased in size in comparison to the prior study Dec. 18, 2009. A bone scan at end of each cycle showed multiple metastases within the cervical, thoracic and upper lumbar spine, anterior and posterior ribs, left anterior iliac crest and posterior iliac bones. These were mostly unchanged as compared with the base study of Dec. 18, 2009 (before N-methylisoindigo/dexamethasone treatment) except for the following lesions where the radiotracer uptake was slightly less prominent: anterior left second rib, upper thoracic spine and upper ribs posteriorly. These observations are sharply in contrast with observations before N-methylisoindigo treatment when disease aggressively progressed. For example, from Nov. 25, 2008 to Dec. 18, 2008 (4 weeks before N-methylisoindigo treatment), significant disease progression was observed via imagining studies that showed enlarged metastatic lesions throughout the liver, newly identified hilar lymphadenopathy, increased size of prominent retroperitoneal lymph nodes, and increased prominence of several bony metastases.

Although it is not meant to be applied to a single patient; in order to assess target response further, calculations were made using the "Guidelines to Evaluate the Response to Treatment in Solid Tumors (RECIST)" that are used to document tumor size change and monitor treatment response in larger controlled clinical trials. Five liver metastatic tumors at end of third cycle were compared with their baseline before N-methylisoindigo treatment. This was done by calculating percentage decrease of a sum of the longest diameter for all 5 tumors after N-methylisoindigo treatment (3 cycles). As summarized in Table 5, a 26% decrease (1−11.3/15.2%) in a sum of the longest diameters of 5 tumors was obtained. On the basis of the definition provided by NCI guideline (25), this decrease suggested that treatment of N-methylisoindigo plus dexamethasone achieved a stable disease response.

Side Effects

Common side effects related to N-methylisoindigo treatment have been reported previously in patients with chronic myelogenous leukemia, which include muscle pain, GI symptoms (nausea, vomiting, and diarrhea) (27, 28), and headache in healthy volunteers observed in our Phase I clinical trial. These common side effects of N-methylisoindigo did not occur in this patient. There were also no significant changes in hematology and biochemistry. The patient experienced nausea at beginning of N-methylisoindigo study, which was most likely due to Hydrocodone, and it was resolved after termination of Hydrocodone. Other observed adverse effects of N-methylisoindigo-Dexamethasone treatment were fatigue and low blood pressure, which were thought to be related to suppression of high dose Dexamethasone on the adrenal system. (http://emedicine medscape com/article/765753-overview). Otherwise, the patient tolerated the N-methylisoindigo-Dexamethasone therapy well.

TABLE 5

Hepatic Metastases

| Date | Tumor No. | Description | Tumor Size (cm) |
|---|---|---|---|
| Dec. 28, 2009 | Tumor 1 | A right hepatic metastasis to the right the upper inferior vena cava | 2.8 × 2.3 |
| Jan. 27, 2009 | | | 2.3 × 2.0 |
| Mar. 4, 2009 | | | 2.4 × 1.8 |
| Apr. 6, 2009 | | | 2.0 × 1.8 |
| Dec. 28, 2009 | Tumor 2 | A right hepatic lobe metastasis posterior to the distal right hepatic vein | 3.6 × 2.8 |
| Jan. 27, 2009 | | | 2.8 × 2.3 |
| Mar. 4, 2009 | | | 2.7 × 2.2 |
| Apr. 6, 2009 | | | 2.5 × 2.1 |
| Dec. 28, 2009 | Tumor 3 | A left hepatic lobe metastasis anterior to the distal left portal vein | 3.8 × 3.5 |
| Jan. 27, 2009 | | | 2.9 × 2.9 |
| Mar. 4, 2009 | | | 2.9 × 2.8 |
| Apr. 6, 2009 | | | 2.8 × 2.7 |
| Dec. 28, 2009 | Tumor 4 | A posterior inferior right hepatic lobe metastasis | 2.8 × 2.8 |
| Jan. 27, 2009 | | | 2.5 × 2.5 |
| Mar. 4, 2009 | | | 2.4 × 2.3 |
| Apr. 6, 2009 | | | 2.4 × 2.3 |
| Dec. 28, 2009 | Tumor 5 | An anterior/superior left hepatic lobe metastasis | 2.2 × 2.1 |
| Jan. 27, 2009 | | | 1.6 × 1.5 |
| Mar. 4, 2009 | | | 1.6 × 1.5 |
| Apr. 6, 2009 | | | 1.6 × 1.3 |

REFERENCES

1. Pirtskhalaishvili, G., Hrebinko, R. L., and Nelson, J. B. The treatment of prostate cancer: an overview of current options. *Cancer Pract*, 9: 295-306, 2001.
2. Petrylak, D. P., Tangen, C. M., Hussain, M. H., Lara, P. N., Jr., Jones, J. A., Taplin, M. E., Burch, P. A., Berry, D., Moinpour, C., Kohli, M., Benson, M. C., Small, E. J., Raghavan, D., and Crawford, E. D. Docetaxel and estramustine compared with mitoxantrone and prednisone for advanced refractory prostate cancer. *N Engl J Med*, 351: 1513-1520, 2004.
3. Tannock, I. F., de Wit, R., Berry, W. R., Horti, J., Pluzanska, A., Chi, K. N., Oudard, S., Theodore, C., James, N. D., Turesson, I., Rosenthal, M. A., and Eisenberger, M. A. Docetaxel plus prednisone or mitoxantrone plus prednisone for advanced prostate cancer. *N Engl J Med*, 351: 1502-1512, 2004.
4. Taneja, S. S. A multidisciplinary approach to the management of hormone-refractory prostate cancer. *Rev Urol*, 5 Suppl 3: S85-91, 2003.
5. Gao, M., Ossowski, L., and Ferrari, A. C. Activation of Rb and decline in androgen receptor protein precede retinoic acid-induced apoptosis in androgen-dependent LNCaP cells and their androgen-independent derivative. *J Cell Physiol*, 179: 336-346, 1999.
6. Kreis, W., Budman, D. R., and Calabro, A. Unique synergism or antagonism of combinations of chemotherapeutic and hormonal agents in human prostate cancer cell lines. *Br J Urol*, 79: 196-202, 1997.
7. Wang, L. G., Ossowski, L., and Ferrari, A. C. Overexpressed androgen receptor linked to p21WAF1 silencing may be responsible for androgen independence and resistance to apoptosis of a prostate cancer cell line. *Cancer Res*, 61: 7544-7551, 2001.
8. Wang, L. G., Liu, X. M., and Chiao, J. W. Repression of androgen receptor in prostate cancer cells by phenethyl isothiocyanate. *Carcinogenesis*, 27: 2124-2132, 2006.
9. Chou, T. C., Motzer, R. J., Tong, Y., and Bosl, G. J. Computerized quantitation of synergism and antagonism of taxol, topotecan, and cisplatin against human teratocarcinoma cell growth: a rational approach to clinical protocol design. *J Natl Cancer Inst*, 86: 1517-1524, 1994.
10. Nishimura, K., Nonomura, N., Satoh, E., Harada, Y., Nakayama, M., Tokizane, T., Fukui, T., Ono, Y., Inoue, H., Shin, M., Tsujimoto, Y., Takayama, H., Aozasa, K., and Okuyama, A. Potential mechanism for the effects of dexamethasone on growth of androgen-independentprostate cancer. *J Natl Cancer Inst*, 93: 1739-1746, 2001.
11. Gao, Q. Z., Lu, J. J., Liu, Z. D., Zhang, H., Wang, S. M., and Xu, H. Dexamethasone suppresses DU145 cell proliferation and cell cycle through inhibition of the extracellular signal-regulated kinase 1/2 pathway and cyclin D1 expression. *Asian J Androl*, 10: 635-641, 2008.
12. Storlie, J. A., Buckner, J. C., Wiseman, G. A., Burch, P. A., Hartmann, L. C., and Richardson, R. L. Prostate specific antigen levels and clinical response to low dose dexamethasone for hormone-refractory metastatic prostate carcinoma. *Cancer*, 76: 96-100, 1995.
13. Akakura, K., Suzuki, H., Ueda, T., Komiya, A., Ichikawa, T., Igarashi, T., and Ito, H. Possible mechanism of dexamethasone therapy for prostate cancer: suppression of circulating level of interleukin-6. *Prostate*, 56: 106-109, 2003.
14. O'Sullivan, B. T., Cutler, D. J., Hunt, G. E., Walters, C., Johnson, G. F., and Caterson, I. D. Pharmacokinetics of dexamethasone and its relationship to dexamethasone suppression test outcome in depressed patients and healthy control subjects. *Biol Psychiatry*, 41: 574-584, 1997.
15. Yu, H., Kortylewski, M., and Pardoll, D. Crosstalk between cancer and immune cells: role of STAT3 in the tumour microenvironment. *Nat Rev Immunol*, 7: 41-51, 2007.

16. Hodge, D. R., Hurt, E. M., and Farrar, W. L. The role of IL-6 and STAT3 in inflammation and cancer. *Eur J Cancer*, 41: 2502-2512, 2005.

17. Abdulghani, J., Gu, L., Dagvadorj, A., Lutz, J., Leiby, B., Bonuccelli, G., Lisanti, M. P., Zellweger, T., Alanen, K., Mirtti, T., Visakorpi, T., Bubendorf, L., and Nevalainen, M. T. Stat3 promotes metastatic progression of prostate cancer. *Am J Pathol*, 172: 1717-1728, 2008.

18. Paule, B., Terry, S., Kheuang, L., Soyeux, P., Vacherot, F., and de la Taille, A. The NF-kappaB/IL-6 pathway in metastatic androgen-independent prostate cancer: new therapeutic approaches? *World J Urol*, 25: 477-489, 2007.

19. Maitland, N. J. and Collins, A. T. Inflammation as the primary aetiological agent of human prostate cancer: A stem cell connection? *J Cell Biochem*, 105: 931-939, 2008.

20. Narayanan, N. K., Nargi, D., Horton, L., Reddy, B. S., Bosland, M. C., and Narayanan, B. A. Inflammatory processes of prostate tissue microenvironment drive rat prostate carcinogenesis: preventive effects of celecoxib. *Prostate*, 69: 133-141, 2009.

21. Wang, L., Liu, D., Ahmed, T., Chung, F. L., Conaway, C., and Chiao, J. W. Targeting cell cycle machinery as a molecular mechanism of sulforaphane in prostate cancer prevention. *Int J Oncol*, 24: 187-192, 2004.

22. Liu, X. M., Wang, L. G., Li, H. Y., and Ji, X. J. Induction of differentiation and down-regulation of c-myb gene expression in ML-1 human myeloblastic leukemia cells by the clinically effective anti-leukemia agent Methylisoindigo. *Biochem Pharmacol*, 51: 1545-1551, 1996.

23. Ji, X. J., Liu, X. M., Li, K., Chen, R. H., and Wang, L. G. Pharmacological studies of Methylisoindigo: absorption and mechanism of action. *Biomed Environ Sci*, 4: 332-337, 1991.

24. Taneja, S., MacGregor, J., Markus, S., Ha, S., and Mohr, I. Enhanced antitumor efficacy of a herpes simplex virus mutant isolated by genetic selection in cancer cells. *Proc Natl Acad Sci USA*, 98: 8804-8808, 2001.

25. Therasse, P., Arbuck, S. G., Eisenhauer, E. A., Wanders, J., Kaplan, R. S., Rubinstein, L., Verweij, J., Van Glabbeke, M., van Oosterom, A. T., Christian, M. C., and Gwyther, S. G. New guidelines to evaluate the response to treatment in solid tumors. European Organization for Research and Treatment of Cancer, National Cancer Institute of the United States, National Cancer Institute of Canada. *J Natl Cancer Inst*, 92: 205-216, 2000.

26. Venkitaraman, R., Thomas, K., Huddart, R. A., Horwich, A., Dearnaley, D. P., and Parker, C. C. Efficacy of low-dose dexamethasone in castration-refractory prostate cancer. *BJU Int*, 101: 440-443, 2008.

27. Xiao, Z., Hao, Y., Liu, B., and Qian, L. Indirubin and Methylisoindigo in the treatment of chronic myelogenous leukemia in China. *Leuk Lymphoma*, 43: 1763-1768, 2002.

28. Xiao, Z., Qian, L., Liu, B., and Hao, Y. Methylisoindigo for the treatment of chronic myelogenous leukaemia. *Br J Haematol*, 111: 711-712, 2000.

What is claimed is:

1. A method of treating advanced stage prostate cancer, the method comprising administering a compound to a patient in need thereof, wherein the prostate cancer is hormone refractory and/or metastatic and the compound is selected from the group consisting of:

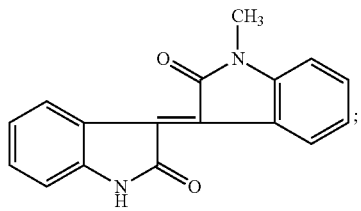

FORMULA (I)

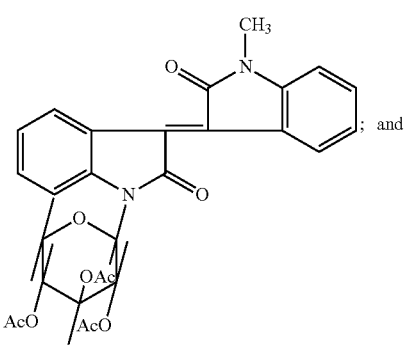

FORMULA (II)

; and

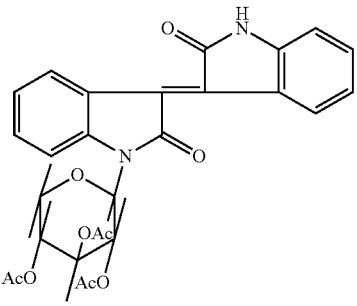

FORMULA (III)

and the compound is in an amount sufficient to inhibit growth, invasion, and/or metastasis of prostate cancer cells.

2. The method of claim 1, wherein the prostate cancer is androgen independent and metastatic prostate cancer and the compound is administered in a pharmaceutical composition comprising a pharmaceutical acceptable carrier.

3. The method of claim 1, wherein the compound is in an amount to induce apoptosis of androgen independent cancer cells.

4. The method of claim 1, wherein the patient is human.

5. The method of claim 4, wherein the compound is in an amount sufficient to inhibit at least 30% of invasive cells.

6. The method of claim 5, wherein at least 60% of the invasive cells are inhibited.

7. The method of claim 1, wherein the compound is administered in combination with paclitaxel or paclitaxel derivatives.

8. The method of claim 1, wherein the compound is administered in combination with dexamethasone.

9. The method of claim 1, wherein the compound is administered in combination with a chemotherapeutic agent, a protein kinase inhibitor, a topoisomerase inhibitor, a mitotic kinesin inhibitor, a histone deacetylase inhibitor, a mTOR inhibitor, a growth factor inhibitor, a growth factor receptor inhibitor, a transcriptional factor inhibitor, an anticancer monoclonal antibody, and/or glucocorticoid hormones.

10. The method of claim 9, wherein the chemotherapeutic agent is selected from the group consisting of: an alkylating agents, anti-metabolitic agents, antibiotics, anti-tubule agents, and anti-hormonal agents.

11. The method of claim 9, wherein the protein kinase inhibitor inhibits at least one of the following: cyclin-dependent kinases, tyrosine kinases, phosphoinositide 3-kinase PI3K/AKT, protein kinase C, casein kinases, MAP kinases, or Src kinases.

12. The method of claim 1, wherein the compound is administered orally.

13. The method of claim 1, wherein the compound is administered parenterally.

14. The method of claim 13, wherein the compound is administered subcutaneously, intravenously, intramuscularly, or intra-arterially.

15. The method of claim 14, wherein the compound is administered to a human patient, in an amount of about 0.5 mg to 5 mg per kilogram of body weight.

16. The method of claim 1, wherein compound is in a dosage unit forms containing between from about 10 mg to about 240 mg of the compound per day.

17. A method of treating advanced stage prostate cancer, the method comprising administering to a patient having hormone refractory and/or metastatic prostate cancer a compound selected from the group consisting of: N-methyl-Δ3,3'-dihydroindole-2,2' diketone; N-1-(β-D-O-triacetyl-xylopranosyl)-Δ3,3'-dihydroindole-2,2' diketone; or N-1-(β-D-O-triacetyl-xylopranosyl)-N'-methyl-Δ3,3'-dihydroindole-2,2' diketone, wherein the compound is in an amount sufficient to inhibit growth, invasion, and/or metastasis of prostate cancer cells.

18. The method of claim 17, wherein the compound is N-methyl-Δ3,3'-dihydroindole-2,2' diketone.

19. The method of claim 18, wherein the compound is N-1-(β-D-O-triacetyl-xylopranosyl)-Δ3,3'-dihydroindole-2,2' diketone.

20. The method of claim 18, wherein the compound is N-1-(β-D-O-triacetyl-xylopranosyl)-N'-methyl-Δ3,3'-dihydroindole-2,2' diketone.

* * * * *